United States Patent [19]

Dietrich et al.

[11] Patent Number: 4,621,104

[45] Date of Patent: Nov. 4, 1986

[54] PROCESS FOR THE PRODUCTION OF LIQUID BROMINE-CONTAINING ALKOXYLATION PRODUCTS

[75] Inventors: Manfred Dietrich, Leverkusen; Manfred Schmidt, Dormagen; Rolf Wiedermann, Odenthal; Klaus König, Leverkusen, all of Fed. Rep. of Germany

[73] Assignee: Bayer Aktiengesellschaft, Leverkusen, Fed. Rep. of Germany

[21] Appl. No.: 785,710

[22] Filed: Oct. 9, 1985

[30] Foreign Application Priority Data

Oct. 20, 1984 [DE] Fed. Rep. of Germany ....... 3438526

[51] Int. Cl.$^4$ .............................................. C08G 18/14
[52] U.S. Cl. .................................... 521/107; 252/182; 521/132; 521/159; 521/171; 524/710; 524/758; 524/792; 528/76; 568/581; 568/614
[58] Field of Search ............... 521/107, 132, 159, 171; 524/710, 758, 792; 528/76; 568/581, 614; 252/182

[56] References Cited

U.S. PATENT DOCUMENTS

| | | | |
|---|---|---|---|
| 3,292,191 | 12/1966 | Kamborian | 12/145 |
| 3,366,557 | 1/1968 | Foulke et al. | 204/49 |
| 3,764,546 | 10/1973 | Feltzin et al. | 252/182 |
| 3,839,465 | 10/1974 | Schneider et al. | 260/615 B |
| 4,020,024 | 4/1977 | Walraevens et al. | 260/2.5 AP |
| 4,128,532 | 12/1978 | Eimers et al. | 528/79 |

FOREIGN PATENT DOCUMENTS

| | | |
|---|---|---|
| 2241156 | 8/1972 | Fed. Rep. of Germany . |
| 1350425 | 3/1963 | France . |
| 115797 | 10/1978 | Japan . |

*Primary Examiner*—Maurice J. Welsh
*Attorney, Agent, or Firm*—Gene Harsh; Joseph C. Gil; Lyndanne M. Whalen

[57] ABSTRACT

Liquid bromine-containing alkoxylation products of butyne-(1,4)-diol which are storage stable are produced. More specifically, 1.5 to 2.5 mols alkylene oxide are reacted with each mol of butyne-(1,4)-diol present at elevated temperature in the presence of a catalyst. The catalyst is selected from (1) thioethers having a molecular weight of up to 5000 obtained by adding a mercaptan and/or mercaptoalcohol to an unsaturated hydrocarbon and/or (2) thioethers other than those of (1) having a molecular weight of from 500 to 5000 and/or (3) alkali metal chlorides. This alkoxylation product is then reacted with bromine at $-10°$ to $80°$ C. The bromide is reoxidized with aqueous hydrogen peroxide solution, stabilized with a relatively non-volatile epoxide and dehydrated. The product thus obtained is particularly useful in the production of flame resistant isocyanate addition products such as polyurethane foams.

18 Claims, No Drawings

PROCESS FOR THE PRODUCTION OF LIQUID BROMINE-CONTAINING ALKOXYLATION PRODUCTS

BACKGROUND OF THE INVENTION

This invention relates to a process for the production of a liquid, bromine-containing alkoxylation product.

Polyurethane and polyisocyanurate foams have numerous and varied applications in the fields of civil engineering, interior decoration and insulation. The flame-resistance of the materials used in such applications is an important property. As legislative regulations relating to fire behavior become more strict, the search for materials which meet these stringent legislative standards has intensified.

Several methods for rendering polyurethane foams flame-resistant are known. In one known process noncombustible additives (such as antimony oxide) or halogenated and/or phosphorus-containing compounds (such as tris-(dibromopropyl)-phosphate or tris-(dichloropropyl)-phosphate, chlorinated biphenyls and halogenated hydrocarbons are added to the foam. However, such additives are not incorporated into the polymer framework and do not produce lasting and homogeneously-distributed flame-resistance. Furthermore, such additives generally have a plasticizing effect on the foam and thereby impair the foam's mechanical properties, particularly pressure-resistance and dimensional stability.

In another method for the production of flame-resistant polyurethane foams, halogenated and/or phosphorus-containing polyols are used. The halogen may be either aromatically or aliphatically bound. However, experience has shown that aromatically bound halogen, as described, for example in U.S. Pat. No. 4,128,532 does not provide good flame-protection, possibly due to the high dissociation energy of the halogen-carbon bond. Such compounds have a relatively high melting point.

French Pat. No. 1,350,425 discloses use of halogenated polyether polyols (produced by addition of epichlorohydrin to polyvalent monomeric alcohols containing at least two hydroxyl groups) in the production of polyurethanes. The cellular polyurethanes obtained by reacting organic polyisocyanates with such halogenated polyether polyols have satisfactory flame-resistant properties but their dimensional stability is only moderate. Furthermore, such polyether polyols are unstable when stored in the presence of amine compounds such as those typically used in the production of polyurethane foams. This instability may be attributed to the fact that hydrogen halide cleaves off very easily from the aliphatic halogen compounds (unlike the aromatic halogen compounds).

It is known that markedly improved flame protection may be achieved by using bromine rather than chlorine: A bromine-containing polyether obtained by alkoxylating dibromobutene diol is disclosed in U.S. Pat. No. 3,764,546. Dibromobutene diol has the advantage that it does not cleave off hydrogen halide as easily as the aliphatic halogen compounds disclosed in French Pat. No. 1,350,425. In the process disclosed in U.S. Pat. No. 3,764,546 the dibromobutene diol is introduced into a polyol and is subsequently alkoxylated by acid catalysis. This process suffers from several disadvantages. For example, the dibromobutene diol must be produced in pure form. Although it is possible to produce such a diol in pure form, the bromination of butynediol in a solvent, filtration, recrystallization and drying is relatively costly. Further, the dibromobutene diol produced in this manner has to be redissolved for alkoxylation. This makes the entire synthesis substantially more difficult. A further disadvantage is that not only the dibromobutene diol but also any remaining polyol mixture is reacted during alkoxylation. Consequently unreacted dibromobutene diol remains. This diol can be filtered off after the reaction, but the diol which remains in the product precipitates when blowing agents conventionally used in rigid foam formulations are added.

According to German Offenlegungsschrift No. 2,445,571, halogenated polyether polyols are obtained by reacting dibromobutene diol with epichlorohydrin. Good flame-protection can be achieved with these products. However, the relatively high viscosity of the products is disadvantageous during processing (particularly metering). The synthesis of these halogenated polyether-polyols is also very costly. In addition to the problems which arise during production of alkoxylation products of dibromobutene diol, a chlorohydrin must be converted into an oxirane (with the cleaving of HCl gas) which is opened by alkaline hydrolysis in order to obtain the desired hydroxyfunctional compound.

In another process (JP No. 78 115 797) for the production of bromine-containing polyols, butynediol is reacted with propylene oxide in the presence of an acid catalyst and then halogenated with bromine. This method is disadvantageous because only about 75 to 80% of the butynediol is reacted during alkoxylation of the butynediol at the desired minimal mol masses (i.e. 1 mol of butynediol reacted with from 1.5 to 2.5 mols of alkoxide). (See Examples 4, 5, 10 and 11 infra.) A very wide isomer spectrum is also obtained when an acid catalyst is employed. In contrast there are essentially only two isomers which are formed when an alkaline catalyst is used. (See Examples 4 and 5 infra). When free butynediol is halogenated to produce 2,3-dibromobutene diol by subsequent bromination, the 2,3-dibromobutene diol partially precipitates immediately (Example 10) or after the addition of a blowing agent. This precipitation problem in particular hinders the use of these products.

The incomplete reaction of butynediol with alkoxides can be avoided if an alkaline catalyst is used instead of an acid catalyst, as described in U.S. Pat. Nos. 3,366,557 and 3,292,191. However, the alkaline catalysts have a tendency to cause a higher stage of hydroxyalkylation and to catalyze the reverse reactions. Consequently, unreacted butynediol or too highly hydroxyalkylated butynediol is often found in the end product. The presence of unreacted butynediol may cause explosions under alkaline conditions due to the instability of the butynediol. Too highly hydroxyalkylated butynediol renders the product so impure that it is no longer usable in many fields. The use of amines as basic catalysts would not overcome these disadvantages because the relatively high temperatures which are required lead to an increased tendency of the butynediol to form by-products and to explosively decompose.

German Offenlegungsschrift No. 2,036,278 discloses use of basic ion exchanger resins as basic agents. These basic ion exchanger resins have substantially improved the selectivity of the reaction but do not eliminate the remaining disadvantages of a basic process such as reverse reaction and risk of decomposition.

German Offenlegungsschrift No. 2,241,156 discloses a process in which thiodialcohols with a low mol composition (particularly thiodiglycol) are used as catalysts. This process suffers from the disadvantage that compounds such as thiodiglycol tend to form readily volatile thioethers under the reaction conditions. Such thioethers give the product such as unpleasant smell that use of the product becomes questionable. Conventional means for eliminating smell, such as hydrogen peroxide treatment, are unsuccessful in this case so that the products which have been catalyzed in this manner have an unacceptable smell. Moreover, thiodiglycol is not an optimal catalyst. The alkoxylation product of 1 mol of butynediol with 2 mols of ethylene oxide still contains a relatively large quantity of the starting material butynediol (See Example 13 infra).

There are as yet no known processes for providing an odor-free alkoxylation product with a low mol composition and a low monomer content (low butyne-1,4-diol content) from butynediol and alkoxides. Moreover, there is no commercially useful synthesis of the corresponding brominated products.

The use of 2,3-dibromobutene-1,4-diol as the starting diol (U.S. Pat. No. 3,764,546) is uneconomical for the reasons discussed above. The method disclosed in Japanese No. 78 115 797 cannot be applied in the described manner because it does not produce neutral products. The bromination of alkoxylation products of butynediol produces a substantial quantity of hydrogen bromide in a secondary reaction which cannot be suppressed. This hydrogen bromide must be removed by neutralization and filtration. This seriously complicates the synthesis and renders it more expensive. Experience has also shown that such bromination products are not stable in storage. Thus, over a period of a few days to weeks a marked rise in the acid number (a fall of the pH value) is observed. This change in the pH value is caused by traces of weakly-bound bromide which is slowly cleaved off as hydrogen bromide during storage. This change in pH value makes it necessary to continually modify processing conditions.

It can be seen from the prior art that different methods are known for producing bromine-containing polyols. However, none of these methods is a straightforward synthesis for liquid bromine-containing products which are stable in storage and are low in 2,3-dibromobutene-1,4-diol.

SUMMARY OF THE INVENTION

It is an object of the present invention to provide a process for the production of liquid bromine-containing alkoxylation products of butyne-(1,4)-diol which are storage stable.

It is also an object of the present invention to provide a process for the production of liquid bromine-containing alkoxylation products of butyne-(1,4)-diol which are relatively odor free.

It is a further object of the present invention to provide an economical and straightforward process for the production of liquid bromine-containing alkoxylation products of butyne-(1,4)-diol in high yield.

It is yet another object of the present invention to provide a process for making flame resistant isocyanate addition products with bromine-containing alkoxylation products of butyne-(1,4)-diol which do not have a detrimental effect upon the mechanical properties of the isocyanate addition product.

These and other objects which will be apparent to those skilled in the art are accomplished by reacting 1.5 to 2.5 mols of alkylene oxide with each mol of butyne-(1,4)-diol at elevated temperature in the presence of a catalyst. The catalyst is selected from (1) thioethers having a molecular weight of up to 5000 obtained by adding a mercaptan and/or mercaptoalcohol to an unsaturated hydrocarbon and/or (2) thioethers other than those of (1) having a molecular weight of from 500 to 5,000 and/or (3) alkali metal chlorides. The resultant alkoxylation product is then reacted with 0.6 to 1.9 mols of bromine for each mol of butyne-(1,4)-diol which had been alkoxylated at a temperature of from −10° to 80° C. The bromide thus formed is reoxidized with an aqueous hydrogen peroxide solution, stabilized with 0.3 to 3 wt % relatively non-volatile epoxide and dehydrated. The bromine-containing alkoxylation product of butyne-(1,4)-diol thus obtained may then be reacted with an isocyanate and a high molecular weight compound containing isocyanate-reactive hydrogen atoms to produce a flame resistant isocyanate addition product.

DETAILED DESCRIPTION OF THE INVENTION

The present invention relates to a process for the production of liquid, bromine-containing alkoxylation products of butyne-(1,4)-diol which have a low content of 2,3-dibromobutene-(1,4) diol and which are stable in storage. In this process, butyne-(1,4)-diol is reacted with an alkylene oxide in the presence of particular catalysts and subsequently brominated. The hydrogen bromide produced in a secondary reaction is converted into reactive bromine and the end product is stabilized. More specifically, butyne-(1,4)-diol is reacted at elevated temperatures with an alkylene oxide in the presence of a catalyst in quantities such that from 1.5 to 2.5 mols, preferably with from 1.98 to 2.05 mols of alkylene oxide (preferably ethylene oxide and/or propylene oxide) are present for each mol of butyne-(1,4)-diol. The catalyst employed is selected from (a) relatively high molecular weight thioethers with a molecular weight of from 500 to 5000 (e.g. thioethers obtained by condensing thiodiglycol, preferably acidically condensing thiodiglycol with concentrated phosphoric acid) and/or (b) thioethers obtained by addition of mercaptans and/or mercapto alcohols (preferably thiodiglycol) to unsaturated hydrocarbons, or the condensation products thereof, which have a molecular weight of up to 5000, and/or (c) alkali metal chlorides. The resulting alkoxylation product is low in butyne-(1,4)-diol content and is reacted at a temperature of from −10° to 80° C. (preferably from 0° to 40° C., most preferably from 5° to 25° C.) with from 0.6 to 1.9 mols (preferably from 0.98 to 1.02 mols) of bromine for each mol of butynediol subjected to alkoxylation. The hydrogen bromide produced in a secondary reaction is converted into reactive bromine by reverse oxidation with aqueous hydrogen peroxide solution. A relatively non-volatile epoxide compound (preferably in a quantity of from 0.3 to 3 wt. %) is added to stabilize the bromination product. The brominated end product may be dehydrated either after being treated with aqueous hydrogen peroxide solution or after addition of the stabilizing epoxide.

This invention also relates to a polyisocyanate polyaddition process for the production of flame-resistant isocyanate addition products such as polyurethane plastics in which these bromine-containing alkoxylation products of butynediol are used, optionally in admixture with other flameproofing agents.

The reaction of butyne-(1,4)-diol with from 1.5 to 2.5 mols of alkylene oxides can not be catalyzed with acidic compounds such as $BF_3$ because molecules with relatively low molecular weights are obtained. From 15 to 20% of the butynediol used would remain in the reaction mixture (see Examples 4 to 10 infra), which butynediol would disturb the subsequent bromination Among the catalysts useful in the reaction of butyne-(1,4) diol with an alkylene oxide are polythioethers with a molecular weight of from 500 to 5000 which can be obtained by condensing thiodiglycol. These relatively high molecular weight or chain-like polythioethers (the production and properties of which are described in German Auslegeschrift No. 1 039 232) have an advantage over low molecular weight thiodiglycols (described, e.g. in German Offenlegungsschrift No. 2 241 156) because the odor which clings to the products made with the high molecular weight polythioethers can be removed by oxidation with hydrogen peroxide. In comparison, it is virtually impossible to remove the odor from products made with low molecular weight thioethers. Further, these catalysts of the present invention yield an alkoxylation product in which there is substantially less free butyne-1,4-diol than when low molecular weight thiodiglycols are employed.

Other catalysts useful in the present invention may be obtained by adding mercaptoalkanes, particularly mercaptoethanol, to compounds containing double bonds. These compounds have no unpleasant odor which would prevent their use. The reaction product of 2 mols of mercaptoethanol with 1 mol of limonene (1-methyl-2-(2-hydroxyethylthio)-4-[1-methyl-2-(2-hydroxyethyl-thio)ethyl]cyclohexane) is a particularly suitable catalyst. This reaction product can, of course, also be condensed to produce relatively high molecular weight units, preferably having a molecular weight of up to 5000.

Alkali metal chlorides particularly potassium chloride may also be used as catalysts for the reaction of butyne-(1,4)-diol with an alkylene oxide. These catalysts also cause the butynediol to be almost completely reacted and result in a product which does not have an unpleasant smell. However, the alkali metal chlorides suffer from the disadvantage that they must be removed from the reaction mixture by filtration. For this reason, the thioethers are the preferred catalysts of the present invention.

As discussed above, suitable thioethers may be obtained in a straightforward manner by condensing thiodiglycol. Acidic etherification using phosphoric acid or phosphoric acid derivatives has proven particularly advantageous for this purpose because it does not produce thioxanes or dithianes which would give the product a very unpleasant smell (German Auslegeschrift No. 1,039,232). The degree of etherification allowed can be easily controlled by the duration of reaction or by the quantity of water which has been cleaved off.

Appropriate thioethers may also be produced by the radical addition of mercaptans or mercaptoethanols to double bonds. Departing from known syntheses, a process is disclosed in U.S. Pat. No. 4,013,724 in which no radical starters (such as azobisisobutyronitrile (AIBN), benzoyl peroxide etc.) which only become active at elevated temperatures are used. Rather the radical-forming effect of atmospheric oxygen is used to synthesize the desired thioethers from the mercaptans or mercaptoethanols and unsaturated systems. The condensation process to produce relatively high molecular weight units is carried out in accordance with techniques known to those in the art.

The butynediol is alkoxylated with from 1.5 to 2.5 mols of alkylene oxide for each mol of butynediol at elevated temperature in the presence of catalytically effective quantities of the aforementioned catalysts such as from 0.1 to 3 wt. % preferably from 0.1 to 1 wt.% of total weight. The alkoxylation products obtained in this manner are then reacted with bromine at a temperature of from $-10°$ C. to 80° C., preferably from 0° C. to 40° C., and most preferably at from $+5°$ C. to 25° C.

From 0.6 to 1.9 mols, preferably from 0.98 to 1.02 mols of bromine are used per mol of butynediol. However, the addition of bromine to the triple bond (as described in Japanese No. 78 115 797) is incomplete. A significant quantity (about 10%) of hydrogen bromide is produced in irrepressible secondary reactions. Products obtained in this manner may not therefore be used without neutralization and filtration. Not only does this render the synthesis more expensive, it also contributes to additional environmental pollution (by the relatively high yield of salt from neutralization).

Bromination is however substantially simplified in the process of the present invention. The hydrogen bromide produced in the bromine addition of the present invention is reoxidized to bromine by addition of an approximately equivalent quantity or slightly excess quantity (about 15% excess) of hydrogen peroxide. Because there are sufficient triple bonds of butynediol present in the reaction mixture, this bromine immediately adds itself to them. The hydrogen bromide is not wasted in the synthesis but is simultaneously added to the triple bond as bromine to complete the addition reaction. The temperature during such bromination is preferably from 0° C. to 40° C., preferably from 5° C. to 25° C. This method, that is the in situ production of bromine by oxidation of HBr using oxidizing agents, is known in principle (German Offenlegungsschrift No. 3 133 577), but until now was only tested on pure butynediol. This oxidation of hydrogen bromide is however surprisingly successful in the presence of the alkoxylated butynediols without causing a cleavage at the ether bond.

The water produced during the reaction of hydrogen peroxide with HBr can easily be removed under vacuum. Dehydration may also be carried out after the addition of epoxide.

Known bromination products are not stable in storage. Small quantities of weakly-bound bromine remain after bromination. This weakly-bound bromine is cleaved off after several days or weeks as hydrogen bromide. Such products can not therefore be used after a certain period because the increased acid number modifies the reactivity and disturbs amine-catalysis in the production of isocyanate addition products such as polyurethane foams.

This increase of free hydrogen bromide or the rise in the acid number during storage is prevented in the present invention by addition of relatively non-volatile epoxide compounds for stabilization. Appropriate epoxide compounds may be obtained, for example, by reacting epihalohydrins (such as epichlorohydrin) with polyfunctional phenols or alcohols. Appropriate polyfunctional phenols include 2,2-bis-(4-hydroxyphenyl)-propane; 1-(4-hydroxyphenyl)-1-(2-hydroxyphenyl)-propane; 3,3-bis-(3-hydroxyphenyl)-pentane; 2-(3-hydroxyphenyl)-2-(4-hydroxyphenyl)-pentane; 1-(2-hydroxyphenyl)-1-(3-hydroxyphenyl)-1-phenyl-propane; 1,1-bis-(4-hydroxyphenyl)-1-phenylbutane; hydroquinone and alkylated hydroquinones. Appropriate alcohols include ethylene glycol, propylene glycol, hexane diol, pentaerythritol or the higher homologs thereof, such as polyethylene glycol and polypropylene glycol.

Such epoxide compounds have the advantage that they quickly react with existing HBr to produce the corresponding bromohydrins and they remain in the product for a long period due to their relative non-volatility. The relatively non-volatile epoxide compounds (such as Levepox 4020 ®, a product and registered trade mark of BAYER AG, D 5090 Leverkusen), are used in a quantity of from 0.3 to 3 wt.%, based on total weight. The molecular weights of such relatively non-volatile epoxides are generally more than 174, preferably more than 300.

The brominated alkoxylation products of butynediol, produced by the above-described process have the advantage that they are liquid, odor-free or slightly odorous products which are stable in storage and have a low content of 2,3-dibromobutene-(1,4)-diol. These products are exceptionally suitable for the production of flame-resistant polyurethane plastics due to their simple production and manageability.

The present invention also relates to the use of the bromine-containing alkoxylation products in a process for the production of polyisocyanate-based flame-resistant plastics, preferably flame-resistant PU-foams, including polyisocyanurate-foams. More specifically, organic polyisocyanates are reacted with relatively high molecular weight compounds having NCO-reactive groups with reactive H-atoms such as OH—, NH$_2$—, NHR—, COOH and/or SH groups (preferably relatively high molecular weight polyhydroxyl compounds), optionally water and/or lower molecular weight chain lengthening agents or cross-linking agents in the presence of auxiliaries and additives and catalysts (including trimerization catalysts) conventionally used in polyurethane chemistry. The bromine-containing alkoxylation products produced by the process of the present invention are used in a quantity of from 1 to 60 wt. % of the relatively high molecular weight compound with isocyanate-reactive groups, optionally in admixture with other flameproofing agents. From 1 to 60 wt. %, preferably from 3 to 50 wt. %, particularly from 5 to 40 wt. % of the bromine-containing polyol prepared in accordance with the present invention is introduced into the relatively high molecular weight isocyanate-reactive group containing (preferably polyol) component.

Of course, a so-called prepolymer can first be produced with the isocyanate component, which prepolymer is used for further reactions.

Polyurethane(urea) foams are conventionally produced within a NCO-characteristic number range of from 100 to 135. However, the characteristic number range can also be above 135 (e.g. up to 500), particularly if the foams are produced using trimerization catalysts for NCO isocyanurate group-containing polyurethane foams (preferred characteristic number range 135 to 500).

Incorporated or external flameproofing agents may also be used as flameproofing agents in addition to the bromine-containing alkoxylation products of butyne-(1,4)-diol of the present invention. Such flameproofing agents are known, and include, for example: trichloroethylphosphate, trichloropropylphosphate, diphenylcresylphosphate, tricresylphosphate, halogenated hydrocarbons and halogenated aromatic materials, such as decabromodiphenylether or even ammonium phosphates and polyphosphates, phosphonic acid esters, such as methyl phosphonic acid dimethylester or esters obtained for example, according to German Offenlegungsschrift No. 2 75 0555 or phosphoric acid esters (German Auslegeschrift No. 1 181 411). Amines according to German Offenlegungsschrift No. 2 406 163 can also be used as incorporated flame-proofing agents. From 3 to 25 wt.%, based on the total weight, of phosphorus-containing and/or halogen (particularly bromine) containing, incorporated or external flameproofing agents are preferably used in addition to the bromine-containing alkoxylation products of the present invention if amines are used.

The production of isocyanate-based plastic materials, is known and described, for example, in German Offenlegungsschriften No. 1 694 142, 1 694 215 and 1 720 768 and in the Kunststoff-Handbuch Vol. VII, Polyurethane, published by Vieweg and Hochtlen, Carl Hanser Verlag (Munich 1966) and in the view edition of this book, published by G. Oertel, Carl Hanser Verlag (Munich/Vienna 1983). These disclosures are primarily concerned with urethane- and/or isocyanurate- and/or allophanate- and/or uretdione- and/or urea- and/or carbodiimide group-containing plastics. The present invention is, however, preferably carried out in the production of polyurethane and polyisocyanurate plastics, particularly foams.

Starting Materials For the Production of Isocyanate-Based Plastics

Aliphatic, cycloaliphatic, araliphatic, aromatic and/or heterocyclic polyisocyanates are known from a plurality of publications to be useful in the synthesis of polyurethanes. Such publications include W. Siefken in Justus Liebigs Annalen der Chemie 562, pages 75 to 136 (1949) and German Offenlegungsschriften No. 2 854 384 and 2 920 501. Such isocyanates can be used as relatively low molecular weight di- or polyfunctional isocyanates or they may be used for the production of relatively low or relatively high molecular weight isocyanate group-containing prepolymers. The following are specific examples of polyisocyanates which may be used in the present invention: ethylene-diisocyanate, 1,4-tetramethylene diisocyanate, 1,6-hexamethylene diisocyanate, 1,12-dodecane diisocyanate, cyclobutane-1,3-diisocyanate, cyclohexane-1,3- and -1,4-diisocyanate and any mixtures of these isomers; 1-isocyanato-3,3,5-trimethyl-5-isocyanato-methyl-cyclohexane, 2,4- and 2,6-hexahydrotoluylene diisocyanate and any mixtures of these isomers; hexahydro-1,3- and/or -1,4-phenylenediisocyanate; perhydro-2,4'- and/or -4,4'-diphenylmethane-diisocyanate; 1,3- and 1,4-phenylenediisocyanate; 2,4- and 2,6-toluylene diisocyanate and any mixtures of these isomers; diphenylmethane-2,4'-, 2,2'- and/or 4,4'-diisocyanate; naphthylene-1,5-diisocyanate; triphenylmethane-4,4',4''-triisocyanate; polyphenyl-polymethylene-polyisocyanates (obtained by aniline-formaldehyde condensation and subsequent phosgenation as described in British Pat. Nos. 874 430 and 848 671); perchlorinated arylpolyisocyanates (described in German Auslegeschrift No. 1 157 601); carbodiimide group-containing polyisocyanates (German Patentschrift No. 1 092 007); diisocyanates (U.S. Pat. No. 3,492,330); allophanate group-containing polyisocyanates (British Patent No. 994,890, Belgian Pat. No. 761 626 and Published Dutch Patent Application No. 7 102 524); isocyanurate group-containing polyisocyanates (German Patentschriften Nos. 1 022 789, 1 222 067 and 1 027 394, and German Offenlegungsschriften Nos. 1 929 034 and 2 004 048); urethane group-containing polyisocyanates (Belgian Pat. No. 752 261 and U.S. Pat. No. 3,394,164); acylated urea group-containing polyisocyanates (German Patentschrift No. 1 230 778); biuret group-containing polyisocyanates (German Patentschrift No. 1 101 394, British Pat. No. 889 050 and French Patent No. 7 017 514); polyisocyanates produced by telomerization reactions (Belgian Pat. No. 723 640); ester group-containing polyisocyanates (British Pat. Nos. 965 474 and 1 072 956, U.S. Pat. No. 3,567,763 and German Patentschrift No. 1 231 688); and reaction products of the aforementioned isocyanates with acetals (German Patentschrift No. 1 072 385). It is also possible to use any mixtures of these polyisocyanates.

The commercially easily obtainable polyisocyanates, such as 2,4- and 2,6-toluylene diisocyanate and any mixtures of these isomers ("TDI"), polyphenyl-polymethylene-polyisocyanates, as produced by aniline formaldehyde condensation and subsequent phosgenation ("crude MDI"); 4,4'- and/or 2,4'-diphenylmethane-4,4'-diiosocyanate and carbodiimide group-, urethane group-, allophanate group-, isocyanurate group-, urea group- or biuret group-containing polyisocyanates ("modified polyisocyanates") are preferably used.

The polyisocyanates can also be used in a stabilized form with retarded reactivity, as described in German Offenlegungsschriften Nos. 3 112 054, 3 228 723, 3 228 724, 3 228 670 and 3 230 757 and European Patent Application No. 2 230 757.

Relatively high molecular weight compounds having at least two groups with isocyanate-reactive hydrogen atoms and a molecular weight of generally from 400 to 10,000 may be used as starting components in the production of polyisocyanate addition products in accordance with the claimed invention. Such compounds include hydroxyl-, amino group-, thiol group- or carboxyl group-containing compounds. Hydroxyl group-containing compounds, particularly those containing two to eight hydroxyl groups and having a molecular weight of from 1000 to 5000 (preferably from 800 to 3000) are preferred compounds having isocyanate-reactive hydrogen atoms. These preferred compounds include, for example, polyesters, polyethers, polythioethers, polyacetals, polycarbonates and polyester amides and other relatively high molecular weight compounds known for the production of homogeneous and cellular polyurethanes containing at least two, generally from 2 to 8, preferably from 2 to 4 hydroxyl groups. Specific examples of these preferred compounds are listed in German Offenlegungsschriften Nos. 2 920 501 and 2 854 384.

The hydroxyl group-containing polyesters which may be used are, for example, reaction products of polyvalent (preferably divalent and optionally additionally trivalent) alcohols with polyvalent (preferably divalent) carboxylic acids, polycarboxylic acid anhydrides or polycarboxylic acid esters of lower alcohols. The polycarboxylic acids can be of an aliphatic, cycloaliphatic, aromatic and/or heterocyclic nature and are optionally substituted by, for example, halogen atoms and/or are unsaturated. The following are specific examples of appropriate acids, anhydrides and esters: succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, oleic acid, dimeric and trimeric fatty acids, optionally in combination with monomeric fatty acids, terephthalic acid dimethyl esters and terephthalic acid-bis-glycol esters. Ethylene glycol, propane-(1,2)-and-(1,3)-diol, butane-(1,4)-and-(2,3)-diol, hexane-(1,6)-diol, octane-(1,8)-diol, neopentyl glycol, 1,4-bis-hydroxymethylcyclohexane, 2-methylpropane-1,3-diol, glycerin, trimethylol propane, hexane-(1,2,6)-triol, butane-(1,2,4)-triol, trimethylol ethane, pentaerythritol, quinitol, mannitol, sorbitol, 1,4,3,6-dianhydrohexites, methyl-glycoside, di-, tri-, tetra- and polyethylene glycol, di-, tri-, tetra- and polypropylene glycol and di-, tri-, tetra- and polybutylene glycol, for example, may be used as polyvalent alcohols. The polyesters can proportionally contain terminal carboxyl groups. Polyesters made up of lactones, such as ε-caprolactone or hydroxycarboxylic acids, such as ω-hydroxycaproic acid may also be used.

The polyesters containing at least two, generally from two to eight, preferably from two to three, hydroxyl groups useful in the practice of the present invention are known and may be obtained for example by polymerization of tetrahydrofuran and/or epoxides (such as ethylene oxide, propylene oxide, butylene oxide, styrene oxide or epichlorohydrin) on their own in the presence of BF$_3$, or by adding these epoxides (optionally in admixture or in succession) to starting components having reactive hydrogen atoms. Suitable starting compounds include water; alcohols such as ethylene glycol, propane-(1,3)-or-(1,2)-diol, trimethylol propane, 4,4'-dihydroxy-diphenyl propane; amines such as aniline or ethylene diamine; ammonia; amino alcohols such as ethanol amine; and sugar. Sucrose polyethers, as described, for example, in German Auslegeschriften Nos. 1 176 358 and 1 064 938 may also be used in the practice of the present invention. Relatively high molecular weight polyoxyalkylenepolyols, such as polyoxytetramethylene glycols or ethoxylation- and/or propoxylation-products of lower molecular weight di- and polyols or mono-, di- and polyamines, such as propoxylated trimethylol propane, propoxylated ethylene diamine or straight or branched polypropylene glycol ethers, (which can contain proportions of ethylene oxide in statistical, block or terminal form and in total have a molecular weight of from 400 to 10,000 (preferably from 600 to 6,000)) are among the polyethers useful in the present invention. Vinylpolymer-modified polyethers, as produced, for example, by polymerizing styrene and acrylonitrile in the presence of polyethers (U.S. Pat. Nos. 3,383,351, 3,304,273, 3,523,093 and 3,110,695, German Patentschrift No. 1 152 536) are also suitable, as are OH group-containing polybutadienes. Polyethers having secondary OH groups are preferred as suspension media.

Appropriate polythioethers include in particular the condensation products of thiodiglycol with itself and/or with other glycols, dicarboxylic acids, formaldehyde, amino-carboxylic acids or amino alcohols.

Compounds produced from glycols, such as diethylene glycol, triethylene glycol, 4,4'-diethoxydiphenyl-dimethylmethane, hexane diol and formaldehyde, for example, can be used as polyacetals. Polyacetals which are suitable to the present invention may also be produced by polymerization of cyclic acetals.

Known polycarbonates which can be produced by reacting phosgene with diols, such as propane-(1,3)-diol, butane-(1,4)-diol and/or hexane-(1,6)-diol, di-, tri- or tetraethylene glycol and diaryl carbonates such as diphenyl carbonate can also be used as hydroxyl group-containing polycarbonates.

Substantially linear condensates, produced from polyvalent saturated and unsaturated carboxylic acids or the anhydrides thereof and polyvalent saturated and unsaturated amino alcohols, diamines, polyamines and mixtures thereof may be used as polyester amides and polyamides. Urethane or urea group-containing polyhydroxyl compounds and optionally modified, natural polyols such as castor oil, carbohydrates or starch may also be used. Addition products of alkylene oxides to phenol-formaldehyde resins or to urea-formaldehyde resins may also be used in the process of the present invention.

Hydroxyl end group-containing polybutadienes are also suitable. These polybutadienes produce particularly elastic and hydrolysis-stable products. Polyhydroxyl compounds in which high molecular weight polyadducts or polycondensates or prepolymers are contained in finely-dispersed form or even in solution can optionally also be used. Such polyhydroxyl compounds may be obtained by carrying out polyaddition reactions (for example reactions between polyisocyanates and aminofunctional compounds) or polycondensation reactions (for example between formaldehyde and phenols and/or amines) in situ in the aforementioned hydroxyl group-containing compounds. Such processes are described in German Auslegeschriften Nos. 1 168 075 and 1 260 142, and German Offenlegungsschriften Nos. 2 324 134, 2 423 984, 2 512 385, 2 513 815, 2 550 796, 2 550 797, 2 550 833, 2 550 860, 2 550 862, 2 633 293 and 2 639 254 and U.S. Pat. No. 3,869,413.

Vinylpolymer-modified polyhydroxyl compounds such as those obtained by polymerizing styrene and acrylonitrile in the presence of polyethers (U.S. Pat. Nos. 3,383,341, 3,304,273, 3,523,093, 3,110,695; German Auslegeschrift No. 1 152 536) or polycarbonate polyols (German Patentschrift No. 1 769 795; U.S. Pat. No. 3,637,909) are also suitable for the process of the present invention. If polyether polyols which are modified according to German Offenlegungsschriften Nos. 2 442 101, 2 644 922 and 2 646 141 by graft polymerization with vinylphosphonic acid esters and optionally (meth-)acrylonitrile, (meth)-acrylamide or OH-functional (meth)acrylic acid esters are used, plastic materials with exceptional flame-resistance are obtained. Polyhydroxyl compounds into which carboxyl groups have been introduced by radical graft polymerization using unsaturated carboxylic acids and optionally further olefinically unsaturated monomers (German Offenlegungsschriften Nos. 2 714 291, 2 739 620 and 2 654 746) can advantageously be used in conjunction with mineral fillers.

If such modified polyhydroxyl compounds are used as starting components in the polyisocyanate polyaddition process, polyurethane plastics which have substantially improved mechanical properties are often produced.

Further examples of these compounds containing isocyanate reactive hydrogen atoms which may be used in the present invention are described, for example, in High Polymers, Vol. XVI, "Polyurethanes, Chemistry and Technology", by Saunders Frisch, Interscience Publishers (New York/London), Vol. I, 1962, pages 34-42 and pages 44 and 54 and Vol. II, 1964, pages 5-6 and 198-199 and in the Kunststoff-Handbuch, Vol. VII, Vieweg-Hochtlen, Carl-Hanser-Verlag, (Munich), 1966, e.g. on pages 45 to 71 and in German Offenlegungsschriften Nos. 2 854 384 and 2 920 501.

Of course mixtures of the aforementioned compounds having at least two isocyanate-reactive hydrogen atoms with a molecular weight of from 400 to 10,000 (e.g. mixtures of polyethers and polyesters) can also be used.

Low-melting (<60° C.), relatively high molecular weight polyamines having aromatic and/or aliphatic amino groups and a molecular weight of from 400 to 10,000, (preferably from 500 to 6,000), can also be used as relatively high molecular weight compounds having NCO-reactive hydrogen atoms.

Polyamino compounds which are produced by (preferably basic) hydrolysis, particularly by hydrolyzing suitable relatively high molecular weight polyhydroxyl compound and excess aromatic diisocyanate-based NCO-prepolymers are suitable as relatively high molecular weight polyamino compounds having aromatic amino groups with a molecular weight of from 400 to 10,000, preferably from 500 to 6,000. Examples of this hydrolysis process are given in German Offenlegungsschriften Nos. 2 948 419, 3 039 600 and 3 112 118; European Patent Application Nos. 61 627, 71 132 and 71 139. German Offenlegungsschrift No. 29 48 419 also discloses other prior art processes for the production of aromatic amino compounds with a relatively high molecular weight structure suitable for the process of the present invention. These disclosures are directed to polyether-polyamines, but polyester-, polyacetal-, polythioether- or polycaprolactone-polyamines (preferably 2- or 3-functional polyamines) which contain urethane groups (from the reaction of the corresponding relatively high molecular weight polyhydroxyl compounds with the excess polyisocyanates) and support the amino groups on the radical of the (former) polyisocyanate can also be used.

Aromatic, relatively high molecular weight polyamines can also be produced by other processes. For example, NCO-prepolymers may be reacted with excess quantities of aminophenyl- ethyl amine, or other diamines (German Auslegeschrift No. 1 694 152). In another possible synthesis, (described in French Pat. No. 1 415 317), NCO-prepolymers are converted with formic acid into N-formyl derivatives and saponified. The reaction of NCO-prepolymers with sulfaminic acid (German Auslegeschrift No. 1 155 907) produces relatively high molecular weight polyamines.

Amino group-supporting relatively high molecular weight polyamino compounds which are bound (via aliphatic polyisocyanates) to aliphatic radicals in addition to amino group-supporting relatively high molecular weight polyamine compounds (aromatic polyisocyanates) which are bound to aromatic radicals can also be used in the practice of the present invention.

Relatively high molecular weight aliphatic di- and polyamines obtained by reductive amination of polyoxyalkylene glycols with ammonia (Belgian Pat. No. 634 741 or U.S. Pat. No. 3,654,370) can also be used. Other relatively high molecular weight polyoxyalkylene-polyamines may be produced by methods such as those disclosed in the company journal "Jeffamine, Polyoxypropylene Amines" by Texaco Chemical Co., 1978. Cyanethylated polyoxypropylene glycols may be hydrogenated (German Offenlegungsschrift No. 1 193 671). Polypropylene glycol sulphonic acid esters may be aminated (U.S. Pat. No. 3,236,895). A polyoxyalkylene glycol may be treated with epichlorohydrin and a primary amine (FR No. 1 466 708). NCO-prepolymers may be reacted with hydroxyl group-containing enamines, aldimines or ketimines and subsequently hydrolyzed (German Offenlegungsschrift No. 2 546 536). Suitably relatively high molecular weight aliphatic di- and polyamines also include the polyamines obtained (according to German Offenlegungsschriften Nos. 29 48 419 and 3 039 600) by alkaline hydrolysis of NCO-prepolymers (with aliphatic diisocyanates) with bases via the carbamate state. These relatively high molecular weight polyamines have a molecular weight of from about 400 to 10,000, preferably from 500 to 6,000 and most preferably from 1,000 to 3,000.

The polyurethane plastics produced in accordance with the present invention are optionally produced with relatively low molecular weight chain lengthening agents or cross-linking agents. These relatively low molecular weight chain lengthening agents or cross-linking agents include di- or poly-functional compounds, which contain hydroxyl groups (polyols) bound to aliphatic and/or cycloaliphatic groups and/or $NH_2$ groups (polyamines) bound to aromatic (including heterocyclic) rings having an aromatic character and having a molecular weight of from 62 to 399. Lower molecular weight diols having hydroxyl groups bound to aliphatic or cycloaliphatic groups and aromatic diamines with a molecular weight of from 108 to 399 are preferred.

These chain-lengthening or cross-linking agents generally have from 2 to 8, preferably from 2 to 4, most preferably 2, isocyanate-reactive hydrogen atoms, such as hydroxyl and/or amine groups. Of course mixtures of different compounds can also be used. The following are specific examples of such compounds: ethylene glycol, trimethylene glycol, butane-2,3- and/or -1,4-diol, hexane-1,6-diol, neopentyl glycol, 1,4-bis-hydroxyethylcyclohexane, 1,4-dihydroxycyclohexane, terephthalic acid-bis ($\beta$-hydroxyethyl)ester, 1,4,3,6-dianhydrohexites and 1,4-mono-anhydrotetrites. Less preferred diols are those having secondary hydroxyl groups, such as propylene glycol, butane-2,3-diol and pentane-2,5-diol. The following are examples of polyvalent chain-lengthening or cross-linking agents: trimethylol propane, trimethylol ethane, hexane-1,2,6-triol, glycerin, pentaerythritol, quinitol, mannitol, sorbitol, castor oil and di-, tri- and tetra-ethylene, -propylene, and -butylene glycols, also bis-(2-hydroxyethyl)-hydroquinone, bis-(2-hydroxyethyl)-resorcinol, formose and formitol. Tertiary amine-containing di- or polyols, such as N-methyldiethanolamine, triethanolamine or N,N'-bis-hydroxyethyl-piperazine are also suitable. However, polyamines, preferably diamines can also be used.

Those amines which contain the amino group bound to heterocyclic radicals having an aromatic character are also to be understood as aromatic polyamines. The following are examples of suitable aromatic polyamines: p-phenylene diamine; 2,4-/2,6-toluylene diamine; diphenylmethane-4,4'- and/or -2,4' and/or -2,2'-diamines; 3,3'-dichloro-4,4'-diaminodiphenylmethane; 3-($C_1$–$C_8$)-alkyl-4,4'-diaminodiphenylmethanes; 3,3'-di-($C_1$–$C_4$)-4,4'-diamino-diphenylmethanes; 3,3',5,5'-tetra-($C_1$–$C_4$)-alkyl-4,4'-diamino-diphenylmethanes; 4,4'-diamino-diphenyl-sulfides, -sulfoxides or -sulfones; ether group-containing diamines (German Offenlegungsschriften Nos. 1 770 525 and 1 809 172 (U.S. Pat. Nos. 3,654,364 and 3,736,295)); 2-halogen-1,3-phenylene diamines which are optionally substituted at the 5-position (German Offenlegungsschriften Nos. 2 001 772, 2 025 896 and 2 065 869); bisanthranilic acid esters (German Offenlegungsschriften Nos. 2 040 644 and 2 160 590); 2,4-diaminobenzoic acid esters (German Offenlegungsschriften No. 2 025 900); and toluylene diamines substituted by one or two ($C_1$–$C_4$) alkyl groups. 3,5-Diethyl 2,4- and/or -2,6-diaminotoluene (particularly the commercial 80/20 or 65/35 isomer mixtures thereof), unsymmetrically tetraalkyl-substituted diaminodiphenyl methanes (for example, 3,5-diethyl-3'-5'-diisopropyl-4,4'-diaminodiphenyl methane) and the isomer mixtures thereof (German Offenlegungsschrift No. 2 902 090), 4,4'-diaminobenzanilide, and 3,5-diaminobenzoic acid-($C_1$–$C_4$)-alkyl esters, 4,4'- and/or 2,4'-diaminodiphenyl methane, and naphthylene-1,5-diamine are particularly preferred.

However, diols or diamines with additional groups such as adipic acid-bis(2-hydroxyethyl)esters, terephthalic acid-bis-(2-hydroxyethyl)esters, diolurethanes, diolureas or polyols, which contain sulfonate and/or phosphonate groups, such as 1,6-hexa-methylene-bis-(2-hydroxyethylurethane), 4,4'-diphenyl-methane-bis-(2-hydroxyethylurea) or the adduct of sodium bisulfite on butene-1,4-diol or the alkoxylation products thereof may also be used. Other relatively low molecular weight compounds are disclosed in detail in German Offenlegungsschrift No. 2 854 384.

Other examples of chain lengthening agents or cross-linking agents which can optionally also be used in the practice of the present invention include: ethylene diamine; propylene diamine; hexane-1,6-diamine; 2,2,4-trimethyl-1,6-diaminohexane; 2,5-dimethyl-2,5-diamino-hexane; 1,10-decane diamine; 1,11-undecane diamine; 1,12-dodecane diamine; bis-aminomethyl-hexahydro-4,7-methano-indan (TCD-diamine); 1,3-cyclohexane diamine; 1,4-cyclo-hexane diamine; 1-amino-3,3,5-trimethyl-5-aminomethylcyclohexane (isophorone diamine); 2,4- and/or 2,6-hexa-hydrotoluylene diamine; 2,4'- and/or 4,4'-diaminodicyclohexylmethane; m- or p-xylene diamine; bis-(3-aminopropyl)-methylamine; bis-N,N'-(3-aminopropyl)-piperazine; 1-amino-2-amino-methyl-3,3,5-(3,5,5)-trimethylcyclopentane; 2,2-dialkylpentane-1,5-diamines or triamines such as 1,5,11-triaminoundecane and 4-amino-methyl-1,8-diaminooctane; lysine methylesters; cycloaliphatic triamines (German Offenlegungsschrift No. 2 614 244); 4,7-di-oxadecane-1,10-diamine; 2,4- and 2,6-diamino-3,5-diethyl-1-methylcyclohexane and mixtures thereof; alkylated diaminodicyclohexylmethanes (e.g. 3,3'-dimethyl-4,4'-diaminodicyclohexylmethane and 3,5-diisopropyl-3',5'-diethyl-4,4'-diaminodicyclohexylmethane); perhydrogenated diaminophthalenes; perhydrogenated diaminoanthracenes; and relatively high valence amines such as diethylene triamine, triethylene tetramine, pentaethylene hexamine, dipropylene triamine, tripropylene tetramine, or N,N'-dimethyl-ethylene diamine, 2,5-dimethyl-piperazine, 2-methyl-piperazine, piperazine-(hydrate) and 2-hydroxyethyl-piperazine.

The following may also be used as relatively low molecular weight chain lengthening agents: hydrazine (particularly in the form of hydrazine hydrate); $C_1$–$C_6$-alkyl-substituted hydrazines, such as methyl hydrazine, ethyl hydrazine; hydroxy ethyl hydrazine and N,N'- dimethyl hydrazine. Other suitable chain lengthening agents include compounds with hydrazide end groups (e.g., di- or polyhydrazines) such as carbodihydrazide, hydracrylic acid hydrazide, oxalic acid dihydrazide, adipic acid dihydrazide, terephthalic acid dihydrazide, isophthalic acid hydrazide, compounds having hydrazide- and semi-carbazide-, or amino groups such as β-semi-carbazidopropionic acid hydrazide, aminoacetic acid hydrazide and β-aminopropionic acid hydrazide.

From 0.01 to 10 wt.%, based on solid polyurethane, of compounds which are monofunctional with respect to isocyanates can also optionally be used in a conventional manner as so-called chain terminators. Examples of such monofunctional compounds are: monoamines such as butyl or dibutyl amine, stearyl amine, pyrrolidine, 4-amino-2,2,6,6-tetramethylpiperidine, aniline and tolylamine; monoalcohols such as butanol, 2-ethyl-hexanol, cyclohexanol; ethylene glycol monoethyl esters; monooximes such as butanoneoxime; and other monofunctional compounds such as N,N-dimethylhydrazine acetic acid hydrazide and benzoic acid hydrazide.

Conventional polyurethane catalysts, particularly tertiary amines or metal catalysts may be used as catalysts in one-component systems according to the present invention which has stability in long-term storage. Examples of such catalysts are tertiary amines such as triethylamine, tributylamine, N-methyl-morpholine, N-ethyl-morpholine, N-co-comorpholine, N,N,N',N'-tetramethyl-ethylene diamine, 1,4-diazabicyclo-(2,2,2)-octane, N-methyl-N'-dimethyl-aminoethyl-piperazine, N,N-dimethylbenzylamine, bis-(N,N-diethylaminoethyl)-adipate, N,N-diethylbenzylamine, pentamethyl-diethylene triamine, N,N-dimethylcyclohexylamine, N,N,N',N'-tetramethyl-1,3-butane diamine, N,N-dimethyl-β-phenylethylamine, 1,2 dimethylimidazole and 2-methylimidazole.

Examples of isocyanate group-active hydrogen atom-containing tertiary amines are: triethanol amine, triisopropanol amine, N-methyl-diethanol amine, N-ethyl-diethanol amine, dimethyl-ethanol amine, and the reaction products thereof with alkylene oxides, such as propylene oxide and/or ethylene oxide.

Silamines with carbon-silicon bonds (described, for example, in German Patentschrift No. 1 229 290) which can be used as catalysts include 2,2,4-trimethyl-2-silamorpholine and 1,3-diethyl-aminomethyl-tetramethyl disiloxane.

Nitrogen-containing bases such as tetraalkylammonium hydroxides, alkali metal hydroxides such as sodium hydroxide, alkali metal phenolates such as sodium phenolate and alkali metal alcoholates such as sodium methylate may also be used as catalysts. Hexahydrotriazines are also suitable catalysts.

Organic metal compounds, particularly organic tin compounds and lead compounds are also appropriate catalysts. Tin(II) salts of carboxylic acids such as tin(II)-acetate, tin(II)-octoate, tin(II)-ethylhexoate and tin(II)-laurate and the dialkyl tin salts of carboxylic acids such as dibutyl tin diacetate, dibutyl tin dilaurate, dibutyl tin maleate and dioctyl tin diacetate are among the useful organic tin compounds.

Further examples of catalysts which can be used in the practice of the present invention and details about the action of the catalysts are described in the Kunststoff-Handbuch, Vol. VII, published by Vieweg and Hochtlen, Carl-Hanser-Verlag (Munich 1966), e:g. on pages 96 to 102, and in European Patent Application No. 3 230 757.

The catalysts if used are generally used in a quantity of from about 0.001 to 10 wt. %, based on the reactive mixture.

The following are examples of auxiliaries and additives which may optionally be used in the production of isocyanate addition products in accordance with the present invention: dyes or pigments; fillers, such as silica gel, gypsum, talcum, active carbon, metal powder; UV-absorption agents or stabilizers, such as phenolic anti-oxidants; light-protecting agents; blowing agents; surface-active additives such as emulsifiers or foam stabilizers; cell-regulators; anti-blocking agents; silicones; flameproofing agents and fungistatically and-/or bacteriostatically-acting materials. Fiber-materials, i.e. known inorganic and/or organic fibrous reinforcing materials may be used as fillers.

If polyurethane foams are to be produced by the process of the present invention, water and/or readily volatile organic materials are used as blowing agents. Examples of organic blowing agents are: acetone; ethylacetate; methanol; ethanol; halogen-substituted alkanes such as methylene chloride, chloroform, ethylidene chloride, vinylidene chloride, monofluorotrichloromethane, chlorodifluoromethane, dichlorodifluoromethane, -butane, -hexane, -heptane and diethylether.

A blowing effect can also be achieved by addition of compound which decomposes at relatively high temperatures with the separation of gases such as the nitrogen in azo compounds (e.g. azobutyric acid nitrile). Other examples of blowing agents and details about the use of blowing agents, are described in Kunststoff-Handbuch, Vol. VII, published by Vieweg and Hochtlen, Carl-Hanser-Verlag (Munich 1966) on pages 108 and 109, 453 and 455 and 507 to 510.

Surface-active additives (emulsifiers and foam-stabilizers) can be used in the process of the present invention. The sodium salts of castor oil sulfonates or of fatty acids or salts of fatty acids having amine groups such as oleic acid diethylamine and stearic acid diethanol amine, may be used as emulsifiers. Alkali metal or ammonium salts of sulfonic acids (such as of dodecyl benzene sulfonic acid or dinaphthylmethane disulfonic acid) or of fatty acids (such as ricinoleic acid) or of polymeric fatty acids can be used as surface-active additives.

Water-soluble polyethersiloxanes in particular can be used as foam-stabilizers. These compounds are generally structured in such a manner that a copolymer of ethylene oxide and propylene oxide is linked to a polydimethylsiloxane radical. Such foam stabilizers are described in U.S. Pat. No. 2,764,565.

Reaction retarders such as hydrochloric acid or organic acid halides; known cell regulators such as paraffins or fatty alcohols or dimethylpolysiloxanes; pigments or dyes; known flameproofing agents such as tris-choroethylphosphate or ammonium phosphate and -polyphosphate; stabilizers against ageing and the effect of weathering; plasticizers; fungistatically- and bacteriostatically- acting materials; and fillers such as barium sulfate, kieselguhr, carbon black or prepared chalk can also be used.

Other examples of surface-active additives foam-stabilizers, cell regulators, reaction-retarders, stabilizers, flame-retarding substances, plasticizers, dyes, fillers and fungistatically- and bacteriostatically-acting materials which can optionally also be used in accordance with the present invention and details about the use and actions of these additives are given in the Kunststoff-Handbuch, Vol. VI, published by Vieweg and Hochtlen, Carl-Hanser-Verlag (Munich 1966) on pages 103 to 113 and in German Offenlegungsschriften Nos. 2 854 384 and 2 920 501.

The reaction components from which the isocyanate addition products are formed may be reacted in accordance with the known one-stage process, the prepolymer process or the semi-prepolymer process, generally at a characteristic number of from 50 to 300, preferably from 95 to 250, most preferably from 100 to 130. Mechanical apparatus useful in the production of isocyanate addition products are described in U.S. Pat. No. 2,764,565. Details about the processing apparatus useful in the present invention are described in the Kunststoff-Handbuch, Vol. VII, published by Vieweg and Hochtlen, Carl-Hanser-Verlag, (Munich 1966) on pages 121 to 205.

In the production of foam, foaming may be carried out in sealed molds. The reaction mixture is introduced into a mold made of metal such as aluminum or of plastic such as epoxide resin. The foamable reaction mixture foams in the mold and forms the molding. Mold-foaming can be carried out in a manner such that the molding has a cellular structure on its surface or in a manner such that the molding has a compact skin and a cellular core. The process of the present invention may be carried out so that foamable reaction mixture is introduced into the mold in a quantity which fills the mold exactly. However, it is also possible to introduce more foamable reaction mixture into the mold than is required to fill the mold cavity with foam. The latter process is known as "overcharging".

Known "external mold release agents" such as silicon oils, or so-called "internal mold release agents", optionally in admixture with external mold release agents, are often used in mold forming.

Of course, foams can also be produced by block foaming or by the known laminator process.

The products obtained can be used as insulation boards for roof insulation or as automobile parts.

The invention is further illustrated, but is not intended to be limited by the following examples in which all parts and percentages are by weight unless otherwise specified.

EXAMPLES

Catalyst A 5856 parts by weight of thiodiglycol were mixed with 29.3 parts by weight of ortho-phosphoric acid (according to German Auslegeschrift No. 1 039 232). Condensation was carried out until 765 ml of water cleaved off. A water jet vacuum was then applied for 3 hours at 180° C. and a reaction product having an OH-number of 110 was obtained in a 91% yield. The resulting polythioether had a molecular weight of about 1000.

Catalyst B

The same reactants in the same quantities were treated in accordance with the same production process used to produce catalyst A to produce a polythioether with a molecular weight of 2000. However, water (in total 820 ml) had to be separated off for 3 hours longer. A product was obtained which had a molecular weight of about 2000 and an OH-number of 54.

Catalyst C 780 g of 2-mercaptoethanol and 545 g of limonene were stirred in a 2 l round-bottomed flask with simultaneous introduction of air for 24 hours at room temperature. Excess mercaptoethanol was then distilled off under vacuum. A diadduct of mercaptoethanol on limonene was obtained which had the following analytical data:
OH-number 381
Viscosity at 25° C.: 1300 mPas Catalyst C was condensed to produce a polythioether having a molecular weight of about 1100 in the following manner. 4 mols of catalyst C were mixed with 5.8 g of concentrated $H_3PO_4$ and heated for 6 hours under a water jet vacuum to 160° C. 52 g of water distilled off during this time. The product obtained in this matter had an OH-number of 101. The viscosity was 7500 mPas/25° C.

EXAMPLE 1

34.4 kg (400 mols) of butyne-1,4-diol (melting point of ≈58° C.) were melted in a 100 l tank. After addition of 242 g of potassium chloride, 46.4 kg (800 mols) of propylene oxide were metered in at 70° C. under two bars of nitrogen pressure over a period of from 6 to 7 hours. The reaction was subsequently carried out for 5 hours at 80° C. After addition of 80 g of 2,6-di-t-butyl-4-methylphenol, the mixture was degassed under vacuum for 1 hour at 80° C. to remove small quantities of free propylene oxide and then filtered off from precipitated potassium chloride.

Yield: 80 kg

The analytical data of the alkoxylation product were as follows:
OH number: 549
Viscosity at 25° C. (mPas): 149
acid number: 0.1
$H_2O$ (%): 0.05
free butyne diol (%): 0.3

A bromine-containing product was formed from this composition in Example 7.

EXAMPLE 2

104.2 kg (400 mols) of 33% aqueous butynediol were dehydrated in a 100 l tank at no higher than 80° C. under vacuum until the water content was ≦0.5%. After addition of 210 g of polythioether catalyst A (molecular weight of 1000), 36.08 kg (820 mols) of ethylene oxide were metered in over a period of from 5 to 6 hours at 70° C. and under two bars of nitrogen pressure. After a subsequent reaction period of 5 hours at 80° C. and addition of 70 g of 2,6-di-t-butyl-4-methylphenol, the mixture was degassed for 1 hour under vacuum to remove small quantities of unreacted ethylene oxide.

Yield: 70 kg

The analytical data of the alkoxylation product were as follows:
OH number: 619
Viscosity at 25° C. (mPas): 90
acid number: 0.03
$H_2O$ (%): 0.05
free butynediol (%): 0.5

Further processing of this material is described in Example 8.

EXAMPLE 3

104.2 kg (400 mols) of 33% aqueous butynediol were dehydrated in a 100 l tank at no higher than 80° C. under vacuum until it had a water content of ≦0.5%. After addition of 280 g of polythioether catalyst B (molecular weight of 2000), a mixture of 4.4 kg (100 mols) of ethylene oxide and 5.8 kg (100 mols) of propylene oxide were metered in over a period of 2 hours at 70° C. and under 2 bars nitrogen pressure. After a subsequent reaction period of 2 hours, 26.4 kg (600 mols) of ethylene oxide were added over a period of from 5 to 6 hours. After a subsequent reaction period of 5 hours, and addition of 70 g of 2,6-di-t-butyl-4-methylphenol, the mixture was degassed for 1 hour under vacuum to remove small quantities of ethylene oxide.

Yield: 70.5 kg.

The analytical data of the product were as follows:
OH—number: 622
viscosity at 25° C. (mPas): 105
acid number: 0.1
$H_2O$ (%): 0.04
free butynediol (%): 0.6

Further processing of this material is described in Example 9.

EXAMPLE 4

(Comparative Example)

344 g (4 mols) of butynediol were dissolved in 320 g of acetone in a 2 l round-bottomed flask with a stirring device, cooling device, dropping funnel and a thermometer. 348 g (6 mols) of propylene oxide were slowly added dropwise at 20° C. after addition of 2 ml of $BF_3$ etherate. After the acetone had distilled off, an adduct was obtained with an OH number of 651, which contained a further 23 wt. % of free butynediol.

The isomer distribution of the product was as follows:
free butynediol: 23 wt. %
butynediol+1 PO: 34 wt. %
butynediol+2 PO: 26 wt. %
butynediol+3 PO: 16 wt. %

Further processing of this material is described in Example 10.

EXAMPLE 5

In a further test, 344 g (4 mols) of butynediol and 3.5 g of polythioether catalyst A (molecular weight of 1000) were gradually mixed at 70° with 348 g (6 mols) of propylene oxide. After a period of subsequent reaction at 80° C., an adduct with an OH number of 649 was obtained which contained 4.4 wt. % free butynediol. The isomer distribution of the product was as follows:
free butynediol: 4.4 wt. %
butynediol+1 PO: 37.9 wt. %
butynediol+2 PO: 56.2 wt. %
butynediol+3 PO: 1.4 wt. %

EXAMPLE 6

860 g (10 mols) of butyne-1,4-diol were melted in a 5 l flask and, after addition of 8.8 g of catalyst C (1-methyl-2-(2-hydroxyethylthio)-4-(1-methyl-2-(2-hydroxyethylthio)-ethylcyclohexane), 902 g (20.5 mols) of ethylene oxide were metered in over a period of 6 hours at 70° C. and under 0.5 bars of nitrogen. After a subsequent reaction period of 5 hours and addition of 2 g of 2,6-di-t-butyl-4-methylphenol, the mixture was degassed under vacuum for 1 hour at 70° C. to remove small quantities of free ethylene oxide.

Yield: 1760 g.

The analytical data of the product were as follows:
OH—number: 636
viscosity at 25° C. (mPas): 88
acid number: 0.07
$H_2O$ (%): 0.06
free butynediol (%): 0.2

EXAMPLE 7

51.93 kg of the polyether from Example 1 (OH—number: 549; F=2) were placed in a 100 l enamel tank at 10° C. under nitrogen. 40.6 kg of bromine were then metered in such that the temperature did not exceed 20° C. After about 6 h, the addition of bromine was concluded and the mixture was stirred for a further 2 h at 20° C. Corresponding to the content of hydrogen bromide produced, 3.2 kg of a 34% hydrogen peroxide solution (110% of the theoretically required quantity) were then added dropwise with cooling (temp. ≦20° C.). The mixture was stirred for 12 h at room temperature for the subsequent reaction, mixed with 1 kg of epoxide Levepox 4020 ® (BAYER AG, D-5090 Leverkusen) and then dehydrated under vacuum at 70° C. The polyether remained homogeneous and stable and was odor-free.

Yield: 90.7 kg.
Analytical data:
OH—number: 296
acid number: 0.2
pH: 6.8
$H_2O$: 0.05%
viscosity at 25° C.: 580 mPas

EXAMPLE 8

59.00 kg of the polyether from Example 2 (325.5 mols) and 52.08 kg of bromine were reacted in a 100 l tank in the same manner as the reactants in Example 7. The resulting HBr was oxidized with 2.46 kg of 34% hydrogen peroxide solution and then dehydrated at 70° C. under vacuum. 1.1 kg of the epoxide Levepox 4020 ® was used for stabilization. The polyether remained homogeneous and stable and was almost odor free.

Yield: 109 kg.
Analytical data:
acid number: 0.2
OH—number: 325
$H_2O$: 0.05%
pH: 6.9
viscosity at 25° C.: 410 mPas

EXAMPLE 9

50.51 kg of the polyether from Example 3 were reacted with 45.67 kg of bromine according to the procedure described in Example 7. The resulting hydrogen bromide was oxidized with 2.67 kg of 34% hydrogen peroxide solution (10% excess) and dehydrated under a water jet vacuum at 70° C. The mixture was stabilized with 1 kg of Levepox 4020 ®. The polyether remained homogeneous and stable and was almost odor-free.

Yield: 94.5 kg.
Analytical data:
acid number: 0.3
OH number: 320
$H_2O$: 0.1%
pH: 6.5 viscosity at 25° C.: 470 mPas

EXAMPLE 10

(Comparative Example)

606 g of the polyether from Example 4 containing a large quantity of butynediol were reacted with 560 g of bromine at a temperature of from 15° to 20° C. The resulting product was treated with hydrogen peroxide solution in accordance with the procedure described in Example 7, dehydrated and stabilized with Levepox 4020 ®. The dibromobutene diol produced by the reaction with bromine crystallized out after the reaction. The polyether obtained in this manner had, after one day, a pasty consistency and was no longer free-flowing.

EXAMPLE 11

2279 g of the polyether from Example 5 were reacted with 2560 g of bromine at 20° C. The crude product was worked up by the same procedure described in Example 7. 5007 g of a clear product which remained homogeneous and stable even in storage had the following analytical properties:
acid number: 0.3
$H_2O$: 0.12%
OH—number: 307
viscosity at 25° C.: 710 mPas
were obtained.

EXAMPLE 12

1058 g (6 mols) of the polyether from Example 6 were reacted with 960 g of bromine by the procedure described in Example 7. A polyether was obtained in an almost quantitative yield which had the following analytical properties:
acid number: 0.1
OH—number: 323
$H_2O$: 0.2%
viscosity at 25° C.: 450 mPas

EXAMPLE 13

(Comparative Example, alkoxylation according to Example 1 of German Offenlegungsschrift No. 2 241 156)

860 g (10 mols) of butyne-1,4-diol were reacted with 902 g (20.5 mols) of ethylene oxide in the presence of 8.6 g of thiodiglycol at from 55° to 58° C. according to Example 6. 1750 g of the ethoxylated product were obtained. The analytical data for the product were as follows:
OH—number: 634
viscosity at 25° C.: 88 mPas
acid number: 0.07
$H_2O$: 0.1
free butyne-1,4-diol: 2.5%

The alkoxylation product obtained in this manner was reacted with 10 mols of bromine by the same procedure described in Example 7. The resulting product and particularly the waste water produced during distillation had an unpleasant smell. The free dibromobutene diol precipitated out on addition of 20% of Freon 12. (Trademark of DuPont de Nemours, E. I. & Co.).

Examples Illustrating the Production of Polyurethane From the Brominated Polyethers of the Present Invention The following dibromobutene diol polyethers were used to produce foams:
Ether 1 (Example 8): 1 mol of dibromobutene diol + 2.05 mols of ethylene oxide, OH—number 325
Ether 2 (Example 9): 1 mol of dibromobutene diol + 1.75 mols of ethylene oxide + 0.25 mols of propylene oxide, OH—number 320

Foams were produced in the following manner: All components, with the exception of isocyanate, listed in Table 1 were mixed. This mixture was then intensively stirred for 10 sec with the isocyanate. The term "none" or "little" under the heading shrinkage is an indication of the through-hardening of the foams, the term "none" designating better through-hardening.

The behavior of the product foams in fire showed that a composition with phosphorus-containing flame-proofing agents produced a better result in the burning tests (greater flame-resistance) and that a reduced quantity of the bromine-containing alkoxylation product is required to achieve the same result in the burning test when phosphorous-containing flame-proofing agents are included.

TABLE 1

| | Example | | | | |
|---|---|---|---|---|---|
| | 14 | 15 | 16 | 17 | 18 |
| Dimethylcyclohexylamine[1] | 0.3 | 0.5 | 1 | 2 | 1.8 |
| 25% potassium acetate in diethylene glycol[1] | 2 | 2 | — | — | — |
| propylene oxide polyether[1] (started on sugar and water, OH-number 465, functionality 4.3) | 40 | 55 | 45 | 50 | 60 |
| Dimethylmethane phosphonate[1] | — | — | — | 5 | 7 |
| Trichloroethylphosphate[1] | — | 15 | — | — | — |
| Diethyl-N,N—bis-(2-hydroxy-[1] ethyl)-aminomethylphosphate | — | — | — | 15 | — |
| Ether 1[1] | 60 | 30 | — | — | — |
| Ether 2[1] | — | — | 55 | 30 | 33 |
| Silicon stabilizer**[1] | 1 | 1 | 1 | — | 1 |
| Water[1] | — | — | 0.5 | — | 0.5 |
| Trichlorofluoromethane[1] | 40 | 40 | 35 | 35 | 35 |
| 4,4'-diphenylmethane Diisocyanate with polymeric proportions*[1] | 200 | 111 | 114 | 110 | 200 |
| Setting time (sec.) | 60 | 60 | 60 | 60 | 60 |
| Characteristic number | 210 | 226 | 110 | 110 | 110 |
| Apparent density (kg/m³) | 37 | 37 | 26 | 25 | 25 |
| Shrinkage | none | lit. | lit. | lit. | none |
| Flame height (mm) in the Swiss BVD-test[2] | 120 | 128 | 167 | 120 | 167 |
| Fire classification in the BVD-test[2] | V | V | II | V | II |
| Fire classification according to DIN 4102 | B2 | B2 | B2 | B2 | B2 |

*(Desmodur(R) 44-V20, BAYER AG, D-5090 Leverkusen)
**(B 8404 by Goldschmidt/Essen)
[1]parts by weight
[2]BVD: "Brand-Verhutungs-Dienst" from "Bestimmung der Kennziffer gemaß Wegleitung fur Feuerpolizeivorschriften, Prufung von Brennstoffen und Bauelementen (Brennbarkeit und Qualmbildung)" Edition 1976
Mo-2718

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of liquid bromine-containing alkoxylation products of butyne-(1,4)-diol which are storage stable comprising:
(a) reacting each mol of butyne-(1,4)-diol with from 1.5 to 2.5 mols alkylene oxide at elevated temperature in the presence of a catalyst selected from
 (1) thioethers having a molecular weight of up to 5000 obtained by adding a mercaptan and/or mercaptoalcohol to an unsaturated hydrocarbon and/or
 (2) thioethers other than those of (1) having a molecular weight of from 500 to 5,000 and/or
 (3) alkali metal chlorides
to form an alkoxylation product,
(b) reacting the alkoxylation product of (a) with 0.6 to 1.9 mols of bromine for each mol of butyne-(1,4)-diol used in (a) at a temperature of from −10° to 80° C. to form a bromide,
(c) reoxidizing the bromide of (b) with aqueous hydrogen peroxide solution,
(d) stabilizing the bromide with from 0.3 to 3 wt. % relatively non-volatile epoxide and
(e) dehydrating the bromide.

2. The process of claim 1 in which the thioether (2) is the acidic condensation product of thiodiglycol.

3. The process of claim 1 in which the reaction (b) is carried out at a temperature of from 0° to 40° C.

4. The process of claim 1 in which from 0.98 to 1.02 mols of bromine are used in reaction (b) for each mol of butyne-(1,4)-diol used in reaction (a).

5. The process of claim 1 in which the dehydration (e) is carried out after reoxidation (c) and before the stabilization of (d).

6. The process of claim 1 in which the dehydration (e) is carried out after the stabilization of (d).

7. The process of claim 1 in which the thioether of (a)(1) is the addition product of mercaptoethanol and limonene.

8. The process of claim 1 in which the thioether of (a)(2) is the condensation product of concentrated phosphoric acid and thiodiglycol.

9. The process of claim 1 in which from 1.98 to 2.05 mols of ethylene oxide and/or propylene oxide are reacted with each mol of butyne-(1,4)-diol in (a).

10. The process of claim 1 in which the reoxidation (c) is carried out using an equivalent amount or a slight excess of hydrogen peroxide.

11. The process of claim 1 in which the reoxidation (c) is carried out at a temperature of from 0° to 40° C.

12. The process of claim 1 in which the epoxide used in the stabilization (d) has a molecular weight greater than 174.

13. A process for the production of polyisocyanate-based flame-resistant plastics comprising reacting (a) an organic polyisocyanate with (b) a relatively high molecular weight compound having isocyanate-reactive hydrogen atoms in which from 1 to 60 wt. % of the isocyanate-reactive compound (b) is a liquid bromine-containing alkoxylation product produced by the process of claim 1.

14. The process of claim 13 in which from 40 to 99 wt. % of the isocyanate reactive compound (b) is a polyhydroxyl compound.

15. The process of claim 13 in which from 3 to 50 wt. % of the isocyanate-reactive compound (b) is a liquid bromine-containing alkoxylation product produced by the process of claim 1.

16. The process of claim 15 in which the reactants are employed in quantities such that an NCO characteristic number of from 100 to 135 is obtained.

17. The process of claim 15 in which the reactants are employed in quantities such that an NCO characteristic number of from 135 to 500 is obtained.

18. The process of claim 13 in which the reaction mixture further includes from 3 to 25 wt. % phosphorus- and/or halogen-containing flame-proofing agent.

* * * * *